United States Patent [19]

Thompson et al.

[11] 4,036,987

[45] July 19, 1977

[54] CONTROL OF NEMATODES AND OTHER HELMINTHS

[75] Inventors: Malcolm J. Thompson, Baltimore; Julius Feldmesser; William E. Robbins, both of Silver Spring, all of Md.

[73] Assignee: The United States of America as represented by the Secretary of Agriculture, Washington, D.C.

[21] Appl. No.: 631,259

[22] Filed: Nov. 12, 1975

[51] Int. Cl.$^2$ .............................................. A01N 9/20
[52] U.S. Cl. ................................... 424/325; 424/320; 424/DIG. 12
[58] Field of Search ....................... 424/325, DIG. 12

[56] References Cited

U.S. PATENT DOCUMENTS 3,226,293  12/1965  Ursprung .............................. 424/325

FOREIGN PATENT DOCUMENTS 675,149  8/1967  South Africa

*Primary Examiner*—V. D. Turner
*Attorney, Agent, or Firm*—M. Howard Silverstein; William E. Scott; David G. McConnell

[57] ABSTRACT

Some secondary and tertiary straight and branched chain amides and amines were found to be highly lethal to nematodes and other helminths.

21 Claims, No Drawings

CONTROL OF NEMATODES AND OTHER HELMINTHS

This invention relates to the control of nematodes and other helminths and more specifically to the control of these parasites with certain straight and branched-chain amides and amines.

Plant-parasitic nematodes cause damage to crops in the United States estimated at about seven percent of the annual total crop value. At current values, this amounts to about 3 billion dollars.

The effects of nematodes are insidious and hard to detect. Nematode damage symptoms usually develop gradually and are not specific, but rather are associated with reduced yields or with malfunctioning root systems. Nematodes are among the most difficult of all pests to control because the soil mass in which they live serves as a barrier to uniform permeation by nematicides. The soil barrier also hastens degradation of nematicidal substances thus requiring the use of large amounts to attain significant control. These factors make the use of currently available nematicides economically feasible only when the cop is highly valuable.

Another shortcoming in the control of nematodes is the fact that at present there are only 21 nematicides registered and available for use. This number, when compared to the approximately 125 herbicides and 230 insecticides registered for use, indicates the relatively primative state of the art of nematode control. Furthermore, of the 21 registered nematicides, many are restricted to specific uses and cannot be used for general treatment purposes. In addition, some are hazardous to vertebrates. Eight are organophosphates and carbonates which are hazardous not only to vertebrates but also to the surrounding environment.

The difficulty in finding active compounds is partially responsible for the low number of registered nematicides. Out of thousands of compounds tested in both government and industry evaluation programs, relatively few have been found to have effective nematicidal activity. In fact, at the Nematology Laboratory, Agricultural Research Center, Beltsville, Maryland, out of 2500 chemicals screened only 36 (1.4%) were lethal at concentrations of 10 ppm or less to saprophytic nematodes. Of those 36 compounds, 28 were halogenated and, upon secondary testing, all of the compounds were found to be phytotoxic and/or inactive against plant parasitic nematodes.

Consequently, it was very surprising and quite unexpected when we found that the N-substituted alkyl amides and amines of this invention displayed very high nematicidal activity.

Accordingly, one object of this invention is to provide a means for achieving safe, economical control of nematodes and other helminths.

Another object is to provide compounds that are lethal to nematodes and other helminths at an early larval stage of their growth cycle.

A still further object is to provide compounds that are lethal to nematodes and other helminths at concentrations far below those required with presently available materials.

In general, according to this invention certain secondary and tertiary straight and branched chain amides and amines having chain lengths of from 9 to 35 carbon atoms are found to be highly lethal to nematodes and other helminths when said parasites are exposed to the compounds at an early larval stage of their growth cycle. Compounds found to be useful for the purpose of this invention have the following general formulas:

(1)

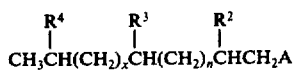

wherein A is selected from the group consisting of

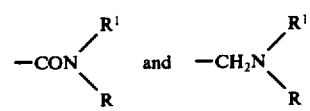

in which R and $R^1$ are individually H, $CH_3$ or $C_2H_5$, and when $x$ and $n$ are each a number 3, each of $R^2$, $R^3$, and $R^4$ are selected individually from the group consisting of H and $CH_3$, and when $x$ and $n$ are not each a number 3 and the total of $x$ and $n$ is a number from 3 to 26, $R^2$, $R^3$, and $R^4$ are hydrogen; and (2)

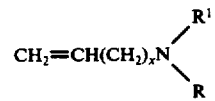

wherein $x$ is a number from 8 to 30, and R and $R^1$ are individually H, $CH_3$, or $C_2H_5$.

More specifically, general formula 1 embodies the following types of compounds that have been found useful for the purposes of this invention:

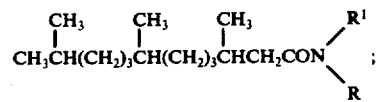

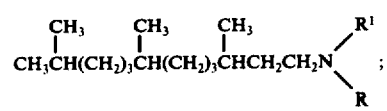

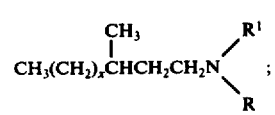

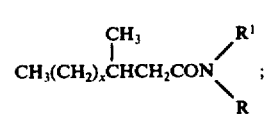

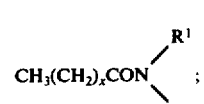

and

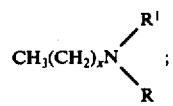

wherein $x$ is a number from 8 to 30, and R and $R^1$ are individually H, $CH_3$, or $C_2H_5$.

The compounds were prepared in 60-80% yield according to the general method of reaction of the appropriate acid with thionyl chloride to give the respective acid chloride which when reacted with the respective low molecular weight amine or ammonia yielded the amide which was reduced to the long chain or branched chain amine with lithium aluminum hydride in tetrahydrofuran. The amines could be in most cases purified via formation of the amine hydrochlorides and by reconversion to the free amines or by column chromatography. The outline of synthesis according to general known method is presented below.

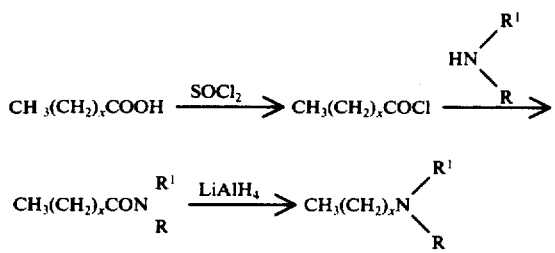

A typical preparation is illustrated by the following detailed example of the synthesis of N,N-dimethyldodecanamide [$CH_3(CH_2)_{10}CON(CH_3)_2$] and N,N-dimethyldodecanamine [$CH_3(CH_2)_{11}N(CH_3)_2$].

A mixture of 30 g of lauric acid (dodecanoic acid), 150 ml of dry benzene and 21.4 g. (13.4 ml) of thionyl chloride was gently refluxed for about 16 hours. The solvent and excess thionyl chloride was removed to yield 32.8 g of the crude acid chloride. To a mechanically stirred solution of the crude acid chloride in 20 ml of dry hexane chilled to 10° C was added 16 g of dimethylamine in 85 ml of hexane. The reaction mixture was removed from the ice bath, stirred for 2 hrs at room temperature, and then filtered. The filtrate was concentrated to dryness under vacuum to give 32 g of crude N,N-dimethyldodecanamide, >95% pure. Trace amounts of the impurity dimethylamine hydrochloride were removed by partitioning the crude dimethylamide between hexane and water. The hexane phase was then dried over sodium sulfate and concentrated to dryness under vacuum, yielding >98% pure N,N-dimethyldodecanamide, $N_D^{19}$ 1.4610.

Crude dimethylamide in 150 ml of dry tetrahydrofuran (THF) was added dropwise to a refluxing solution of 6 g of solid lithium aluminum hydride in 150 ml of THF, and the solution refluxed for about 16 hours, after which two drops of ethyl acetate were added to determine if an excess of lithium aluminum hydride was still present. The reaction mixture was chilled to 10° C, 25 ml of water added dropwise with caution, and then sodium hydroxide, 25 g in 20 ml of water, was added. Upon standing for about 2 hours with occasional stirring and shaking, a gelatinous mass formed and separated from the THF phase. The THF phase was removed and the gelatinous mass rinsed with additional THF. The THF phases were combined and concentrated nearly to dryness under vacuum. The residue was dissolved in hexane and the hexane solution washed with dilute sodium hydroxide, and with water, and then dried over sodium hydroxide pellets. The hexane solution (ca. 300 ml) was treated with a slight excess of a 6 N solution of hydrogen chloride in isopropanol to precipitate out amine hydrochloride which was collected by filtration. The amine hydrochloride was treated with a 3 N sodium hydroxide solution and the amine extracted into hexane. The hexane phase was washed with water, and then dried over sodium hydroxide pellets. Removal of the hexane under vacuum gave 25 g (98%) of N,N-dodecanamine, $n_D^{19}$ 1.4463, > 99% pure.

The compounds were tested by exposing *Panagrellus redivivus*, a saprophytic nematode and a sensitive indicator of nematicidal activity, to them for 48 hours in water-quartz-sand-toxicant mixtures in the standard direct contact test as described in *Plant Dis. Reptr.*, 41, 527, 1957. Each compound was tested at a range of concentrations. The compounds were solubilized in a solvent-surfactant-water medium that is non-toxic to nematodes. The solvent-surfactant-water medium had the following composition: 1 part acetone and 1 part of an aqueous solution containing 5% Tween 20 (polyoxyethylated sorbitan monolaurate) and 5% Triton X-100 (polyoxyethylated octylphenol). Approximately 400 nematodes, in all developmental stages, were exposed in each test. Effects were determined during the day immediately after exposure by microscopic examinations (Soil Science Soc. Fl. Proc. 14, 154, 1954). Normal unstressed *Panagrellus redivivus* are in continuous rapid motion, and the esophageal areas are hyaline, Exposure to nematicides results in reduced motility, immotility, and death, and when the nematodes are moribund or dead the esophageal structures disintegrate and darken. Under these test conditions, the $LD_{95}$ for a standard commercial nematicide, DD (1:1 mixture of 1,2-dichloropropane and 1,3-dichloropropene and related $C_3$ chlorinated hydrocarbons), is 36 ppm, and the lethal dosage is 40 ppm.

As previously stated, in the light of the difficulties experienced in previous searches for chemicals effective in controlling nematodes and other helminths, the activity exhibited by the compounds of this invention was very unexpected and surprising. As shown in Table I, many of the straight chain amides and amines demonstrated very high activity when tested against *Panagrellus redivivus*, a saprophytic nematode. The mono-N-ethyl amide derivatives corresponding to Compounds 1, 2, and 3 were also made, but test results are not recorded in the table because the compounds were not homogeneously dispersed in the test system. This also occurred with Compound 12 and may account for the high concentration required as shown in Table I.

In addition to the straight chain amides and amines in Table I, some branched chain amides and amines were also quite active. For example, N,N-dimethyl-3,7,11-trimethyldodecanamine was active against Panagrellus redivivus at concentrations of from 5 to 10 ppm.

Compounds 2, 9, 17, 19, and 20 were further tested against second stage infective larvae of *Meloidogyne incognita* group, a widespread economically significant root parasite which attacks a large number of cultivated crops. Larvae were directly exposed in a vial test to a range of concentrations of test compounds for 48 hours, and then washed free of the candidate toxicants. Visual examinations showed darkened, disintegrated structures in the esophageal areas of many of the exposed larvae. Viability determinations, however, were made by the following bioassay procedure. Exposed larvae were used to inoculate small nematode-free tomato seedlings (*Lycopersicon esculentum*, var. Rutgers), growing in nematode-free soil in small containers. One thousand exposed nematode Larvae were placed in three or four small holes in the soil around the stem of each tomato seedling. The holes were then tamped shut and the plants were watered lightly, and thereafter maintained on a regular greenhouse schedule. Unexposed larvae were used to inoculate control plants.

*Meliodogyne incognita* causes root galls of "root-knots" in the roots at and adjacent to nematode feeding sites. These galls become macroscopically visible, due to host plant reactions involving the proliferation of abnormally large root cell masses. Infections are evaluated on an arbitrary basis, the "root-knot index," by assigning values of 0 = no infection, 1.0 = 1–25% of the roots galled, 2.0 = 26–50% galled, 3.0 = 51–75% galled, and 4.0 = 100% root infection.

The inoculated tomato seedlings were examined after 3 weeks to determine the viability of the nematode inocula expressed as root infections. Root-knot infections were indexed visually, and the roots were examined microscopically after differential staining to determine the absence or presence of nematodes. The results of inoculation with the exposed root-knot larvae are shown in Table II. The amide, Compound 2, was not effective in preventing root-knot infection at a concentration as high as 100 ppm. However, Compounds 9, 17, and 19 all were very effective in controlling root-knot larvae at 20 ppm. Compound 20 was very effective at 40 ppm and at 20 ppm it prevented >95% of the roots from being infected.

In addition to being active agents for the control of nematodes and other helminths, the compounds of this invention were also found to be active against certain animal-parasitic nematodes at a concentration of 1 ppm and against a free-living flatworm, *Adenoplea* sp., at a concentration of 2.5 ppm.

TABLE I

Range of concentrations of N-substituted amides and amines required to kill 100% of exposed Panagrellus redivivus populations in direct contact tests.

| Compound | | Concentration |
|---|---|---|
| Number | Formula | ppm |
| 1 | $CH_3(CH_2)_9CON(CH_3)_2$ | 20 - 40 |
| 2 | $CH_3(CH_2)_{10}CON(CH_3)_2$ | 5 - 10 |
| 3 | $CH_3(CH_2)_{11}CON(CH_3)_2$ | 5 - 10 |
| 4 | $CH_3(CH_2)_{13}CON(CH_3)_2$ | 20 - 40 |
| 5 | $CH_3(CH_2)_9CON(CH_3)C_2H_5$ | 20 - 40 |
| 6 | $CH_3(CH_2)_{10}CON(CH_3)C_2H_5$ | 20 - 40 |
| 7 | $CH_3(CH_2)_{11}CON(CH_3)C_2H_5$ | 20 - 40 |
| 8 | $CH_3(CH_2)_{10}N(CH_3)_2$ | 5 - 10 |
| 9 | $CH_3(CH_2)_{11}N(CH_3)_2$ | 5 - 10 |
| 10 | $CH_3(CH_2)_{12}N(CH_3)_2$ | 5 - 10 |
| 11 | $CH_3(CH_2)_{14}N(CH_3)_2$ | 5 - 10 |
| 12 | $CH_3(CH_2)_{10}N(CH_3)C_2H_5$ | 40 - 80 |
| 13 | $CH_3(CH_2)_{11}N(CH_3)C_2H_5$ | 5 - 10 |
| 14 | $CH_3(CH_2)_{12}N(CH_3)C_2H_5$ | 5 - 10 |
| 15 | $CH_3(CH_2)_{10}NHC_2H_5$ | 20 - 40 |
| 16 | $CH_3(CH_2)_{11}NHC_2H_5$ | 5 - 10 |
| 17 | $CH_3(CH_2)_{12}NHC_2H_5$ | 5 - 10 |
| 18 | $CH_3(CH_2)_{14}NHC_2H_5$ | <5 |
| 19 | $CH=CH(CH_2)_9N(CH_3)_2$ | 10 - 20 |
| 20 | $CH=CH(CH_2)_9NHC_2H_5$ | 10 - 20 |

TABLE II

Effects of inoculating tomato seedlings with *Meloidogyne incognita* exposed to several concentrations of N-substituted amides and amines for 48 hours.

| Compound | Root-Knot Index | | | Unexposed Control |
|---|---|---|---|---|
| | Concentration ppm | | | |
| | 20 | 40 | 100 | |
| 2 | 2.5 | 2.0 | 2.0 | 3.0 |
| 9 | 0.0 | 0.0 | 0.0 | 3.0 |
| 17 | 0.0 | 0.0 | 0.0 | 3.0 |
| 19 | 0.0 | 0.0 | 0.0 | 3.0 |
| 20 | 1/ | 0.0 | 0.0 | 3.0 |

1/ <5% infected.

We claim:

1. A method of controlling plant parasitic nematodes comprising contacting said nematodes with a lethally effective amount of a compound selected from the group consisting of (a) compounds of the formula

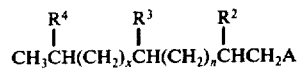

wherein A is

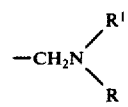

R and $R^1$ are selected from the group consisting of H, $CH_3$, and $C_2H_5$, and when x and n are each a number 3, each of $R^2$, $R^3$, and $R^4$ are selected individually from the group consisting of H and $CH_3$, and when x and n are not each a number 3 and the total of x and n is a number from 3 to 26, $R^2$, $R^3$, and $R^4$ are hydrogen; and (b) compounds of the formula

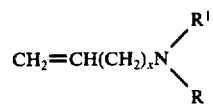

wherein x is a number from 8 to 30, and R and $R^1$ are selected individually from the group consisting of H, $CH_3$, and $C_2H_5$.

2. The method of claim 1 in which the active lethal compound is $CH_3(CH_2)_{10}N(CH_3)_2$.

3. The method of claim 1 in which the active lethal compound is $CH_3(CH_2)_{11}N(CH_3)_2$.

4. The method of claim 1 in which the active lethal compound is $CH_3(CH_2)_{12}N(CH_3)_2$.

5. The method of claim 1 in which the active lethal compound is $CH_3(CH_2)_{14}N(CH_3)_2$.

6. The method of claim 1 in which the active lethal compound is $CH_3(CH_2)_{10}N(CH_3)C_2H_5$.

7. The method of claim 1 in which the active lethal compound is $CH_3(CH_2)_{11}N(CH_3)C_2H_5$.

8. The method of claim 1 in which the active lethal compound is $CH_3(CH_2)_{12}N(CH_3)C_2H_5$.

9. The method of claim 1 in which the active lethal compound is $CH_3(CH_2)_{10}NHC_2H_5$.

10. The method of claim 1 in which the active lethal compound is $CH_3(CH_2)_{11}NCH_2H_5$.

11. The method of claim 1 in which the active lethal compound is $CH_3(CH_2)_{12}NHC_2H_5$.

12. The method of claim 1 in which the active lethal compound is $CH_3(CH_2)_{14}NHC_2H_5$.

13. The method of claim 1 in which the active lethal compound is $CH = CH(CH_2)_9N(CH_3)_2$.

14. The method of claim 1 in which the active lethal compound is $CH = CH(CH_2)_9NHC_2H_5$.

15. The method of claim 1 in which the active lethal compound is

-continued

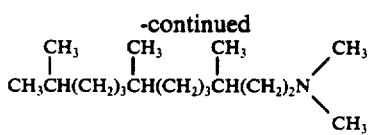

16. A method of controlling damage to crops caused by plant parasitic nematodes, comprising contacting said nematodes with a nematicidal amount of a compound selected from the group consisting of (a) compounds of the formula

wherein A is

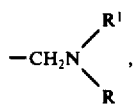

R and R$^1$ are selected from the group consisting of H, CH$_3$, and C$_2$H$_5$, and when $x$ and $n$ are each a number 3, each of R$^2$, R$^3$, and R$^4$ are selected individually from the group consisting of H and CH$_3$, and when $x$ and $n$ are not each a number 3 and the total of $x$ and $n$ is a number from 3 to 26, R$^2$, R$^3$, and R$^4$ are hydrogen; and (b) compounds of the formula

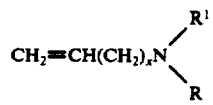

wherein $x$ is a number from 8 to 30, and R and R$^1$ are selected individually from the group consisting of H, CH$_3$, and C$_2$H$_5$.

17. A method of controlling root-knot infection by root parasitic nematodes comprising contacting said parasites with a nematicidal amount of a compound of the formula

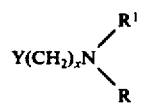

where R and R$^1$ are selected from the group consisting of H, CH$_3$, and C$_2$H$_5$; $x$ is a number from 9 to 12; and Y is selected from the group consisting of CH$_3$ and CH = CH.

18. The method of claim 17 in which the nematicidal compound is CH$_3$(CH$_2$)$_{11}$N(CH$_3$)$_2$.

19. The method of claim 17 in which the nematicidal compound is CH$_3$(CH$_2$)$_{12}$NHC$_2$H$_5$.

20. The method of claim 17 in which the nematicidal compound is CH = CH(CH$_2$)$_9$N(CH$_3$)$_2$.

21. The method of claim 17 in which the nematicidal compound is CH = CH(CH$_2$)$_9$NCH$_2$H$_5$.

* * * * *